United States Patent [19]

Hepp et al.

[11] Patent Number: 4,655,205

[45] Date of Patent: Apr. 7, 1987

[54] DELINEATING AND LIMITING THE ZONE OF SHOCK WAVES FOR THERAPEUTIC PURPOSES

[75] Inventors: Wolfgang Hepp, Immenstaad; Bernd Forssmann, Friedrichshafen; Walter Brendel, Planegg, all of Fed. Rep. of Germany; Christian Chaussy, Los Angeles, Calif.

[73] Assignee: Dornier System GmbH, Friedrichshafen, Fed. Rep. of Germany

[21] Appl. No.: 732,359

[22] Filed: May 8, 1985

[30] Foreign Application Priority Data

May 12, 1984 [DE] Fed. Rep. of Germany ....... 3417710

[51] Int. Cl.⁴ ............................................. A61B 17/22
[52] U.S. Cl. ................................. 128/132 R; 128/328
[58] Field of Search ................ 128/132 R, 804, 328, 128/24 A, 660, 132 D; 250/515.1, 516.1, 519.1; 378/147; 367/150; 73/642

[56] References Cited

U.S. PATENT DOCUMENTS

| 1,574,884 | 3/1926 | Hendricks | 250/515.1 |
| 1,607,140 | 11/1926 | Wappler | 250/515.1 |
| 3,269,173 | 8/1966 | Von Ardenne | 128/660 |
| 3,286,094 | 11/1966 | Pretto | 250/519.1 |
| 3,871,369 | 3/1975 | Krzewinski | 128/132 D |
| 3,937,971 | 2/1976 | Morrison | 250/515.1 |
| 3,942,023 | 3/1976 | Flaugnatti | 250/515.1 |
| 3,950,651 | 4/1976 | Flocee | 378/147 |
| 4,003,383 | 1/1977 | Bruck | 128/804 X |
| 4,122,847 | 10/1978 | Craig | 128/132 R |
| 4,246,791 | 1/1981 | Glenn | 128/660 |
| 4,339,035 | 7/1982 | Marcus | 250/515.1 |
| 4,539,989 | 9/1985 | Forssmann et al. | 128/328 |

FOREIGN PATENT DOCUMENTS

| 2913251 | 10/1980 | Fed. Rep. of Germany | 128/328 |
| 3320998 | 12/1984 | Fed. Rep. of Germany | 128/328 |

Primary Examiner—Clifford D. Crowder
Attorney, Agent, or Firm—Ralf H. Siegemund

[57] ABSTRACT

A template member made of shock wave impermeable material such as air filled foam is affixed to the body of a living being (e.g. a human patient) leaving however an opening through which shock waves from a shock wave generator can pass so that a concrement in the body will be comminuted while the template member shields sensitive organs against parasitic ultrasonic radiation.

9 Claims, 3 Drawing Figures

DELINEATING AND LIMITING THE ZONE OF SHOCK WAVES FOR THERAPEUTIC PURPOSES

BACKGROUND OF THE INVENTION

The present invention relates to a device and arrangement for limiting and delineating the entrance zone for shock waves launched for therapeutic purposes into the body of a living being such as a human patient.

The DORNIER SYSTEM GMBH (assignee) developed a device for contactless comminution of concrement in the body of a living being, such as a human patient, by means of ultrasonic shock waves. The known device is usually comprised of a tub having in its bottom coupled thereto an ellipsoidal reflector which has two focal points. In one of the focal points a spark discharge produces a shock wave, and the reflector focuses the shock waves fronts into the second focal point. The body of the patient is positioned in the tub such that the concrement, for example a kidney stone, is situated in that second focal point. The shock wavefronts as they converge upon this second focal point penetrate into the concrement and cause spalling and comminution to break up the stone into small parts, even grit, which can be discharged from the body by a natural process. German printed patent application No. 3,146,626 (see U.S. Pat. No. 4,539,989) discloses such a device whereby however the tub is replaced by a liquid filled cushion for purposes of acoustically coupling the shock waves from the generating and focusing device into the body.

Upon transmitting shock waves through body tissue the danger arises that certain organs which are sensitive to shock waves such as the lung, the intestinal tract or bones are exposed to shock wavefronts because the comminution process though having an attenuating effect on the focus shock waves nevertheless does not obliterate these shock waves so that following the concentration of shock waves in the second focal point they continue to propagate into further parts of the body. Also, the initial shock wave must be expected to have fringe portions that never reach the second focal point, or the overall construction of the focussing chamber is such that sensitive organs just happen to be in the path of the shock waves regular.

It has to be noted here that the position of various organs in relation to the body surface varies considerably from patient to patient and is in addition dependent upon the position of the patient particularly with respect to the equipment. Moreover, that position may change when the patient moves. The stones and concrements to be comminuted have most certainly not similar position for all various patients. Therefore it seems inevitable that in some cases, depending upon the locating procedure for the concrement prior to the comminution process it happens that sensitive organs are in fact exposed to the shock wave field. This of course is particularly the case if the target is near the lung or the intestinal tract; if the method is used for the decalcificatioon of mitral flap in the heart or for comminuting gall stones shock waves must be expected to reach these sensitive organs.

Another difference to be observed is that simply for reasons of size, the anatomy of children differs from adults therefore special adaptation is needed for the shock wave field to be applied to a child. For this it has been suggested (see Patent Application No. P33 20 998, corresponding to U.S. Pat. No. 4,622,969) to provide diaphragm rings onto the reflector body. This is a viable and practical solution but cannot be deemed to treat the problem exhaustively for reasons of the high degree of complexity in anatomic structure which varies from patient to patient.

DESCRIPTION OF THE INVENTION

It is an object of the present invention to provide a new and improved device and method overcoming the problems outlined above, and to delineate and limit the entrance zone for shock wave into the body of a living being for reliably protecting organs which are sensitive to shock waves.

In accordance with the preferred embodiment of the present invention it is suggested to provide a template like member made of a material which is impermeable or nearly impermeable to acoustic shock waves and to affix this member directly on the body of the human being, there being a well defined opening in that template member for permitting passage of shock waves. Preferably the template member is made of foam material containing pores that can be open or closed. The material should, however, be permeable to X-rays and/or regular ultrasonic waves as used for imaging purposes. A self adhesing layer is provided to affix the template to the body; the opening is particularly adapted to the condition of the organ and may vary from case to case. It is, however, possible to provide for a certain standardization as will be explained below. The template member basically should be easily adaptable for example by a simple procedure of cutting the opening to determine its location, size and configuration.

Generally speaking therefore the invention permits individual adaptation of the shock waves and shock wave field to exactly that zone which must be affected in the body of the living being. Since the template member must be directly affixed to the body, it provides shading for the sensitive areas and zones in the bones and it is noteworthy that even if the shock wave generating and focusing device is not quite correctly positioned, the shading remains effective. Preferably, the template member is caused to adhere to the skin of the patient.

The opening of the template member is just sufficient to expose insensitive areas to the shock waves. This window will be determined in the general sense during a preparation phase of the therapeutic procedure preceding the application proper of the shock wave field. Here one uses known diagnostic techniques such as percussion, excultation, ultrasonic sensing, X-ray techniques or the like in order to pinpoint the location of the concrement and it may well be advisable to provide a marking on the skin of the patient; this marks the spot where the template member is to be applied.

In a advantageous configuration the template member may be chosen in order to adapt to different phases of periodic body functions such as expiration—inspiration or cystolic/diastolic pressure. This procedure depends on whether or not any such particular phases are advantageously used for the application of the therapeutic shock waves, e.g. by serving as trigerring parameters.

The entrance window, of course, must have a fixed and well defined position in relation to the patient and under consideration of the position of the patient during therapy. Here one has to consider the fact that different positions and movements of the patient shift the organs even inside the body, under such a variation and in the direction of effective gravity. All these aspects have to be considered if the patient is subsequently to be treated without danger.

The selection and/or cutting of the template is carried out generally, of course, under consideration of the propagation properties of these shock waves and here particularly whether in the particular area the beams run parallel or divergent or convergent. The template member may be provided with a self adhering layer similar to a bandage to be affixed to the skin in a manner which will avoid any slippage or shifting.

The invention uses the fact that air containing material absorbs or even reflects shock waves to a considerable extent. It is for this reason of advantage to use a foam material which does contain air. The pores can be open or closed as stated. If the shock waves are applied in a water filled hub as was mentioned above, one should use a closed pore foam and of course the adhesion should be resistant against water.

Another factor to be considered is the fact that the shock waves will be generally passed into the body e.g. through some form of water layer coupling medium or the like and/or a gel layer and/or a shock wave permeable membrane contacting the skin through a fatty or oil or other grease layer depending upon the type of equipment (with or without tub) and upon the particular construction. In either case the template member and the adhesion must be resistent against any of these materials.

The inventive template member avoids loading sensitive organs of the patient and is effective independent from adjusting procedures, adjusting errors or unforseeable and basically unavoidable movement by the patient.

The template member should generally be adapted individually to the patient. However it was found that a certain standardization in accordance with patient "types" is possible. In either case, however, it is advisable to make the template member of a material which is easy to cut.

It was mentioned above that locating the concrement is part of the preparatory procedure prior to shock wave application. Generally speaking this locating procedure involves X-rays and it was mentioned above that the template member should be permeable to X-rays. However in order to determine the depth of a concrement underneath the skin ultrasonic imaging techniques may be employed. Therefore this material should be permeable to ultrasonic waves. It has to be observed that the permeability to shock waves is quite distinguishable from permeability to ultrasonic coherent radiation. It was found that polyurethane foam meets all of the requirements for the template.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceding now to the detailed description of the drawings FIG. 1 illustrates a cross section through the body of a patient 2 showing his vertebrae 2a and in addition showing a concrement 8 such as a kidney or a gall stone. Reference numeral 10 and 12 denote generally a certain shock wave sensitive organs in the vicinity of that stone. The equipment for comminution of the concrement—gall stone 8 is basically comprised of a partial ellipsoidal reflector 4 of rotational symmetry and having in one focal point 5 a source for the generation of shock waves such as a spark generator. This reflector 4 is positioned such that its second focal point coincides with the concrement 8.

Figure 1:
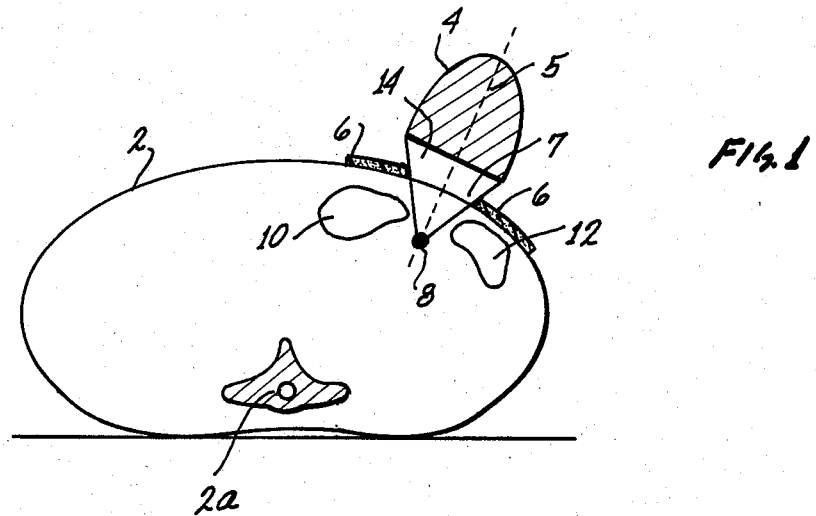
FIG. 1 is a somewhat cross section through the body of a patient as well as through a template member and a shock wave system all in accordance with the preferred embodiment of the present invention for practicing the best mode thereof.

In accordance with the preferred embodiment of the present invention the body in the immediate vicinity of the shock wave applicator is covered by a template member 6 having a particularly situated opening or entrance window 7. It can be seen that this opening is basically positioned in alignment with the axis that runs through the two focal points of the reflector 4.

As now a shock wave is produced in focal point 5 of reflector 4 they will be reflected by the walls of the reflector 4 and run basically in a cone 14 towards the concrement 8. This operation presupposes that the acoustic impedance inside and outside of the body as traversed by the shock waves is substantially the same which condition is attained by providing liquid such as water as coupling fluid between the shock wave generator and the body. This aspect is basically the purpose of the tub mentioned above, or of the employment of a water cushion. Details are omitted here but it is to be understood that basically the zone between the shock wave generator as well as the interior of the reflector up to the skin or surface of the body 2 contains water so that indeed the shock wave cone 14 finds a homogeneous propagation medium throughout.

The opening 7 in the template member 6 is selected i.e. has been made so that the cone 14 will fully traverse that opening while on the other hand the organs 10 and 12 are being shielded or shaded by the material of the template member. Even if for some reason or another the shock wave generator and particularly the focussing chamber 4 is closer or farther from the particular position which, so to speak, is the optimum position as illustrated, still, the shielding function is maintained. In other words the dimensions of the opening 7 is not so much determined by the geometry of the shock wave cone but by the extension of the shock wave sensitive organs 10 and 12 underneath. It is therefore not important if in fact part of the cone, the fringe and outer zones are in fact absorbed by the material 6, these aspects can be taken into consideration when selecting the energy level of shock wave production. The shielding function is clearly of primary concern.

Figure 2:
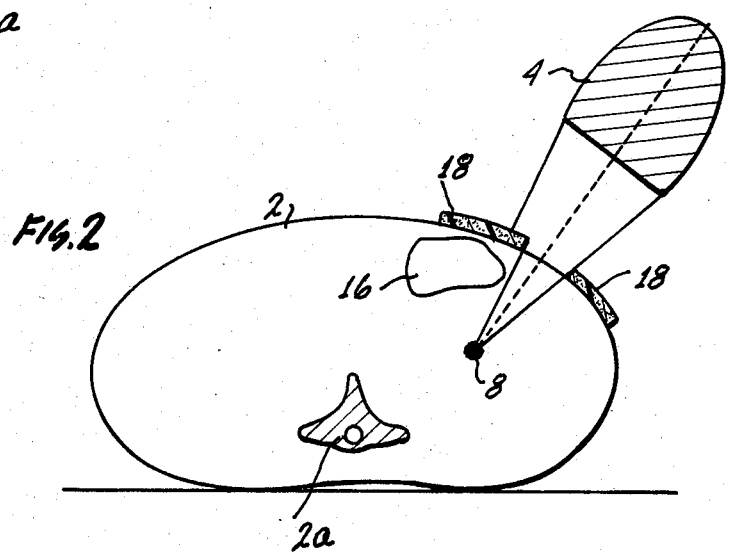
FIG. 2 is a view similar to FIG. 1 but showing a modified shock wave arrangement.

Proceding now to FIG. 2 there is again shown a human body 2 and a particular organ 16 being highly sensitive is very close in relation to the concrement 8' to be comminuted. In this case then the template member 18 is configured for inevitably blocking out part of the shock wave cone in order to make sure the organ 16 is properly shielded and protected against shock waves.

For purposes of facilitating the procedure the ellipsoid 4' in this case is configured as a slightly different focal arrangement; the focal points are further apart and the reflector is positioned somewhat farther away from the skin. Accordingly, the cone is somewhat shallower. This selection and procedure facilitates adequate control of the shielding and shading process by means of the template member 18.

Figure 3:
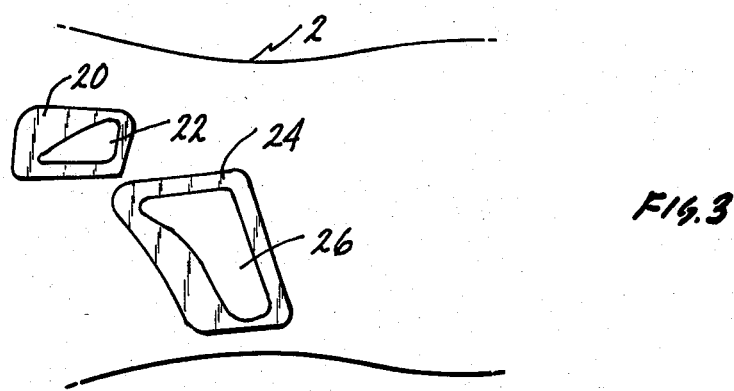
FIG. 3 illustrates in a top elevation two different template members in accordance with the preferred embodiment of the present invention the difference being related to questions of adaptation and is not important in principle.

FIG. 3 illustrates a top elevation of two template members as they are placed in this case on the body of the patient 2. The template member 20 for example has an entrance window 22 which can be described as being pearshaped. This kind of a template will be used in case the procedure relates to the decalcification of the mitral flaps of the heart. Quite clearly the particular template member is critically configured and is provided in this case for protecting lung and stomach of the patient.

The second illustrated template member 24 is provided with a near triangular or foot shaped entrance window 26; one will choose this configuration for a gall stone communication. The upper part of the member 24 protects the chest cavity, including the lungs and the lower part of the colon of the patient.

The outer contour of the template member is of course freely selectable and should be generously provided for and is basically determined by the size and distance of the shock wave reflector or a shock wave transmitter. The template member must be large enough in order to make sure that any fringe radiation and shock waves so to speak are clearly kept away from the patient.

The invention is not limited to the embodiments described above but all changes and modifications thereof, not constituting departures from the spirit and scope of the invention, are intended to be included.

We claim:

1. In a device for therapeutic treatment of the body of a living being by means of shock waves the improvement for limiting the entrance zone for these shock waves, comprising a template member made of shock wave impermeable material and having an adhesive layer thereon for affixing the template directly to the body of the living being, the template having a particularly shaped opening for the passage of shock waves into said body.

2. The improvement as in claim 1 wherein said template member is made of porous foam material containing air.

3. Template member as in claim 1 being made of X-ray permeable material.

4. Template meber as in claim 1 being impermeable to acoustic shock waves but permeable to coherent ultrasonic waves.

5. Template member as in claim 1 including a self adhering layer on the template prior to said affixing.

6. Template member as in claim 1 being made of a material into which said opening can be cut.

7. In a method for comminuting concrements in the body of a living being by means of shock waves comprising the step of
    providing a template member with an aperture and made of shock wave impermeable material;
    adhesively affixing said template member to said body such that sensitive organs are shielded from shock waves, the opening being in alignment with the concrement to be comminuted, and
    directing shock waves through said opening to comminute a concrement.

8. Method as in claim 7 comprising the step of using one of a plurality of standardized template members.

9. Method as in claim 7 and including the step of providing the template member such that it is permeable to at least one of the following, X-rays and coherent ultrasonic waves.

* * * * *